United States Patent [19]

Foller et al.

[11] Patent Number: 5,904,829
[45] Date of Patent: May 18, 1999

[54] METHOD OF CONVERTING AMINE HYDROHALIDE INTO FREE AMINE

[75] Inventors: Peter C. Foller, Murrysville; David G. Roberts, Gibsonia; Robert H. Tang, Murrysville, all of Pa.

[73] Assignee: PPG Industries, Inc., Pittsburgh, Pa.

[21] Appl. No.: 08/914,601

[22] Filed: Aug. 18, 1997

[51] Int. Cl.$^6$ .............................. C25B 1/00; C25B 3/00; C25B 7/00; C25B 9/00

[52] U.S. Cl. .......................... 205/551; 205/552; 205/338; 205/349; 204/537; 204/541; 204/539; 204/630; 204/631; 204/252; 204/257; 204/258; 204/265; 204/253

[58] Field of Search ..................... 204/537, 541, 204/539, 630, 631, 252, 257, 258, 265, 253; 205/431, 551, 552, 338, 349

[56] References Cited

U.S. PATENT DOCUMENTS

| Re. 32,398 | 4/1987 | De Witt et al. ............................ 204/72 |
|---|---|---|
| 596,157 | 12/1897 | Hargreaves .............................. 205/480 |
| 791,194 | 5/1905 | Hoopes .................................... 205/552 |
| 2,049,467 | 8/1936 | Mnookin ................................. 260/127 |
| 2,209,681 | 7/1940 | Kokatnur et al. ............................. 204/9 |
| 2,737,486 | 3/1956 | Bodamer .................................. 204/72 |
| 2,760,979 | 8/1956 | Burghausen ............................ 260/585 |
| 2,769,841 | 11/1956 | Dylewski et al. ....................... 260/585 |
| 3,183,269 | 5/1965 | Costabello et al. ..................... 260/585 |
| 3,202,713 | 8/1965 | Marullo et al. ........................... 260/583 |
| 3,337,630 | 8/1967 | Moke et al. .............................. 260/583 |
| 3,484,488 | 12/1969 | Lichtenwalter et al. ................. 260/585 |
| 3,862,234 | 1/1975 | Steele ................................. 260/585 A |
| 4,024,043 | 5/1977 | Dege et al. ............................. 204/296 |
| 4,116,889 | 9/1978 | Chlanda et al. .......................... 521/27 |
| 4,425,202 | 1/1984 | Sullivan .................................... 204/72 |
| 4,521,285 | 6/1985 | De Witt et al. ........................... 204/72 |

(List continued on next page.)

FOREIGN PATENT DOCUMENTS

WO93/00460  1/1993  WIPO .

OTHER PUBLICATIONS

Hydrina® Membrane Electrolyzers Product Brochure, De Nora Permelec S.p.A., Milano, Italy. no date available.

*Encyclopedia of Chemical Technology*, Kirk–Othmer, Fourth Ed., vol. 8, John Wiley & Sons, Inc., New York (1993), pp. 74–108. no month available.

Ethyleneamine Chlorohydrate Conversion into Ethyleneamine by Electrodialysis on bipolar Ion–Exchange Membranes, Greben, V.P. et al., Translated From: Zhurnal Priklandnoi Khimii, vol. 66, No. 3, pp. 574–578, Mar. 1993, Plenum Publishing Corporation.

(List continued on next page.)

*Primary Examiner*—Arun S. Phasge
*Assistant Examiner*—Edna Wong
*Attorney, Agent, or Firm*—Irwin M. Stein; James R. Franks

[57] ABSTRACT

Describes a method of electreochemically converting amine hydrohalide, e.g., amine hydrochloride, into free amine, e.g., free ethyleneamine. An electrolytic cell is provided having (1) a catholyte compartment containing a cathode assembly comprising a cathode and a bipolar ion exchange membrane, (2) an anode compartment containing an anode assembly comprising either (a) a hydrogen consuming gas diffusion anode and a current collecting electrode or (b) a hydrogen consuming gas diffusion anode which is fixedly held between a hydraulic barrier and a current collecting electrode, and (3) at least one pair of intermediate compartments separating the catholyte and anode compartments and separated from each other by an anion exchange membrane. The following are introduced into the cell: a first aqueous conductive electrolyte solution into the catholyte compartment; hydrogen gas into the anode compartment; an aqueous solution of amine hydrohalide into the first compartment of the pair of intermediate compartments; and a second aqueous conductive electrolyte solution into the second compartment of the pair of intermediate compartments. Direct current is passed through the electrolytic cell, and an aqueous solution comprising free amine is removed from the first compartment.

24 Claims, 3 Drawing Sheets

U.S. PATENT DOCUMENTS

| | | | |
|---|---|---|---|
| 4,561,945 | 12/1985 | Coker et al. | 204/98 |
| 4,582,937 | 4/1986 | Hiraga et al. | 564/498 |
| 4,636,289 | 1/1987 | Mani et al. | 204/182.4 |
| 4,645,579 | 2/1987 | Weiss et al. | 204/182.4 |
| 4,918,233 | 4/1990 | Deeba et al. | 564/479 |
| 4,980,507 | 12/1990 | Mizui et al. | 564/482 |
| 5,084,148 | 1/1992 | Kazcur et al. | 204/95 |
| 5,246,551 | 9/1993 | Pletcher et al. | 204/96 |
| 5,281,311 | 1/1994 | Sharifian et al. | 204/101 |
| 5,290,404 | 3/1994 | Toomey | 204/72 |
| 5,389,211 | 2/1995 | Sharifian et al. | 204/72 |
| 5,411,641 | 5/1995 | Trainham, III et al. | 204/59 R |

OTHER PUBLICATIONS

*Electrodialysis Water Splitting Technology*, Mani, K.N., Aqualytics A Division of the Graver Company, Technical Bulletin. no date available.

Chang, Conversion of Ethylene Diamine Dihydrochloride Into Ethylenediamine by Electrodialytic Water–Splitting, J. of App. Electrochem., pp. 731–736, 1979.

METHOD OF CONVERTING AMINE HYDROHALIDE INTO FREE AMINE

DESCRIPTION OF THE INVENTION

The present invention relates to a method of electrochemically converting amine hydrohalide into free amine. Particularly the present invention relates to an electrochemical method of converting ethyleneamine hydrohalides, e.g., ethyleneamine hydrochlorides, into free ethyleneamines. The present invention also relates to an electrolytic cell having at least one pair of intermediate compartments separated by an anion exchange membrane, and separated from a catholyte compartment by a bipolar ion exchange membrane and from a hydrogen gas anode compartment by either a hydraulic barrier or a hydrogen consuming gas diffusion anode.

A major commercial method of producing free amines, particularly free alkyleneamines, and more particularly free ethyleneamines, involves the reaction of a 1,2-dihaloethane, e.g., 1,2-dichloroethane (EDC), with ammonia to produce the entire family of ethyleneamines, including: ethylenediamine (EDA), diethylenetriamine (DETA), triethylenetetramine (TETA), tetraethylenepentamine (TEPA), pentaethylenehexamine (PEHA), piperazine, i.e., diethylenediamine (DEDA), and 2-amino-1-ethylpiperazine. The reaction of EDC and ammonia is well known and is described U.S. Pat. Nos. 2,049,467, 2,760,979, 2,769,841, 3,183,269, 3,484,488, and 4,980,507.

When the 1,2-dihaloethane reactant is 1,2-dichloroethane, the ethyleneamines are produced as their hydrochloride salts which are subsequently neutralized, typically with an aqueous alkali metal hydroxide, e.g., sodium hydroxide. The neutralization reaction results in the formation of a mixture of free ethyleneamines and by-product alkali metal halide, e.g., sodium chloride. The by-product alkali metal halide salt is typically separated from the mixture of free ethyleneamines by an evaporative or distillation process. The mixture of free ethyleneamines is further individually isolated by fractional distillation. The presence of halide anion, e.g., chloride anion, in the free ethyleneamines requires that the distillation column(s) be fabricated from expensive corrosion resistant materials such as titanium and stainless steel. The waste water resulting from the distillation process is typically treated further for the removal of trace amounts of amines prior to disposal. The formation of ethyleneamines from the treatment of ethyleneamine hydrochlorides with an alkali metal hydroxide, e.g., sodium hydroxide, is described in U.S. Pat. Nos. 3,202,713, 3,862,234, 3,337,630, and 4,582,937.

The commercial method described above can be expensive, particularly with regard to the cost of distillation equipment, utility costs, raw material costs, and the required treatment of waste streams. As a result, such commercial method is typically dedicated to relatively high volume production of free amines, can be expensive to expand, and may not be cost effective for relatively low volume production of free amines.

The operation of an electrodialyzer for the conversion of amine salts into amines is described in the paper, *"Ethyleneamine Chlorohydrate Conversion Into Ethyleneamine by Electrodialysis on Bipolar Ion-Exchange Membranes"*, Greben, V. P. et al, Zhurnal Prikaladoni Khimii, Vol. 66, No. 3, pp. 574–578, March, 1993. The electrodialyzer contains bipolar ion, anion and cation exchange membranes. The described electrodialyzer does not contain a hydrogen gas anode.

Because of the drawbacks of current commercial methods, alternative methods for producing free amines, e.g., free ethyleneamines, that are lower in cost with regard to, capital investment of equipment, raw material costs, and costs for treatment of waste streams are continually being sought.

It has now been discovered that amine hydrohalides can be electrochemically converted into free amines using an electrolytic cell having at least one pair of intermediate compartments separated from the catholyte compartment by a bipolar ion exchange membrane, and separated from the anode compartment by either a hydrogen consuming gas diffusion anode or a hydraulic barrier. The pair of intermediate compartments are separated from each other by an anion exchange membrane, and the hydrogen consuming gas diffusion anode is either (a) fixedly held between the hydraulic barrier and a current collecting electrode or (b) alone in contact with the current collecting electrode.

In accordance with an embodiment of the present invention, there is provided a method of converting amine hydrohalide into free amine comprising:

(a) providing an electrolytic cell having a catholyte compartment containing a cathode assembly; an anode compartment containing an anode assembly; and at least one pair of intermediate compartments separating the catholyte and anode compartments, said pair of intermediate compartments having a first compartment and a second compartment;

(b) introducing a first aqueous conductive electrolyte solution into the catholyte compartment;

(c) introducing hydrogen gas into the anode compartment;

(d) introducing an aqueous solution of amine hydrohalide into the first compartment of the pair of intermediate compartments;

(e) introducing a second aqueous conductive electrolyte solution into the second compartment of the pair of intermediate compartments;

(f) passing direct current through the electrolytic cell; and (g) removing an aqueous solution comprising free amine from the first compartment of the intermediate compartments; the cathode assembly comprising a cathode and a bipolar ion exchange membrane, the bipolar ion exchange membrane having a cation exchange side and an anion exchange side; the anode assembly comprising a hydrogen consuming gas diffusion anode and a current collecting electrode; the first compartment and the second compartment of the pair of intermediate compartments are separated from each other by an anion exchange membrane, the first compartment being defined by the anion exchange side of the bipolar ion exchange membrane and the anion exchange membrane, the second compartment being defined by the anion exchange membrane and the hydrogen consuming gas diffusion anode; provided that when the electrolytic cell has more than one pair of intermediate compartments, each pair of intermediate compartments is separated from its adjacent pair of intermediate compartments by an intermediate bipolar ion exchange membrane having a cation exchange side located on the side of the intermediate bipolar ion exchange membrane that is closer to the catholyte compartment and an anion exchange side located on the side of the intermediate bipolar ion exchange membrane that is closer to the anode compartment.

In accordance with another embodiment of the present invention, there is provided a method of converting amine hydrohalide into free amine comprising the steps as previously recited wherein the anode assembly further comprises a hydraulic barrier, which separates the anode compartment from the second compartment of the pair of intermediate compartments. The hydrogen consuming gas diffusion anode is fixedly held between the hydraulic barrier and the current collecting electrode.

In accordance with a further embodiment of the present invention, there is provided an electrolytic cell comprising: a catholyte compartment containing a cathode assembly; an anode compartment containing an anode assembly; and at least one pair of intermediate compartments separating the catholyte and anode compartments, said pair of intermediate compartments having a first compartment and a second compartment; the cathode assembly comprising a cathode and a bipolar ion exchange membrane, the bipolar ion exchange membrane having a cation exchange side and an anion exchange side; the anode assembly comprising a hydrogen consuming gas diffusion anode and a current collecting electrode; the first compartment and the second compartment of the pair of intermediate compartments are separated from each other by an anion exchange membrane, the first compartment being defined by the anion exchange side of the bipolar ion exchange membrane and the anion exchange membrane, the second compartment being defined by the anion exchange membrane and the hydrogen consuming gas diffusion anode; provided that when the electrolytic cell has more than one pair of intermediate compartments, each pair of intermediate compartments is separated from its adjacent pair of intermediate compartments by an intermediate bipolar ion exchange membrane having a cation exchange side located on the side of the intermediate bipolar ion exchange membrane that is closer to the catholyte compartment and an anion exchange side located on the side of the intermediate bipolar ion exchange membrane that is closer to the anode compartment.

In accordance with yet a further embodiment of the present invention, there is provided an electrolytic cell as recited above wherein the anode assembly further comprises a hydraulic barrier, the hydrogen consuming gas diffusion anode being fixedly held between the hydraulic barrier and the current collecting electrode. The second compartment of the pair of intermediate compartments is separated from the anode compartment by the hydraulic barrier.

The features that characterize the present invention are pointed out with particularity in the claims which are annexed to and form a part of this disclosure. These and other features of the invention, its operating advantages and the specific objects obtained by its use will be more fully understood from the following detailed description and the accompanying drawings in which preferred embodiments of the invention are illustrated and described.

Other than in the operating examples, or where otherwise indicated, all numbers expressing quantities of ingredients or reaction conditions used in the specification and claims are to be understood as modified in all instances by the term "about".

BRIEF DESCRIPTION OF THE DRAWINGS

In FIGS. 1–3, like reference numerals represent the same structural parts, the same solutions, and the same conduits.

DETAILED DESCRIPTION OF THE INVENTION

Figure 1:
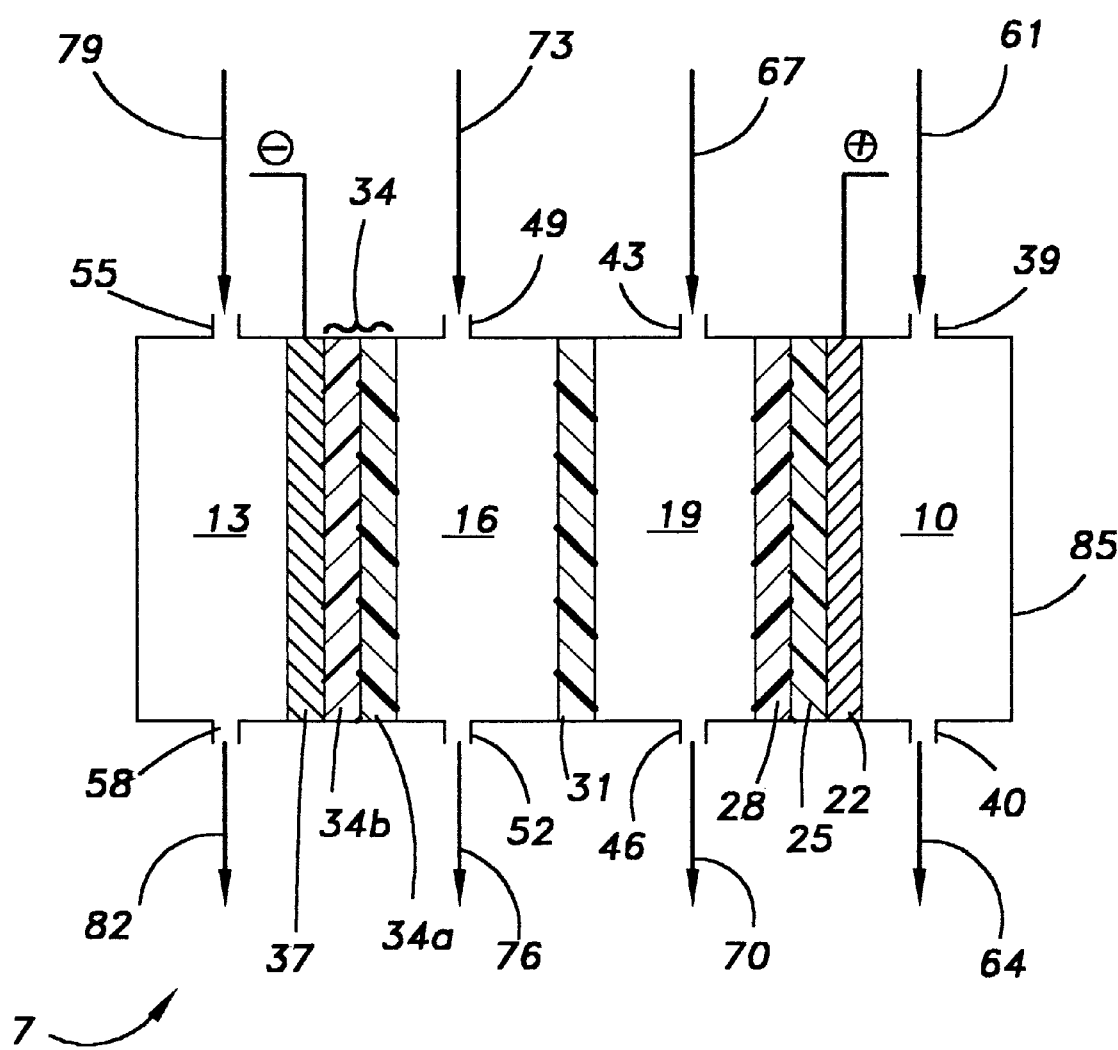
FIG. 1 is a schematic representation of an electrolytic cell useful for converting amine hydrohalide into free amine in accordance with the method of the present invention, which has one pair of intermediate compartments.
Figure 2:
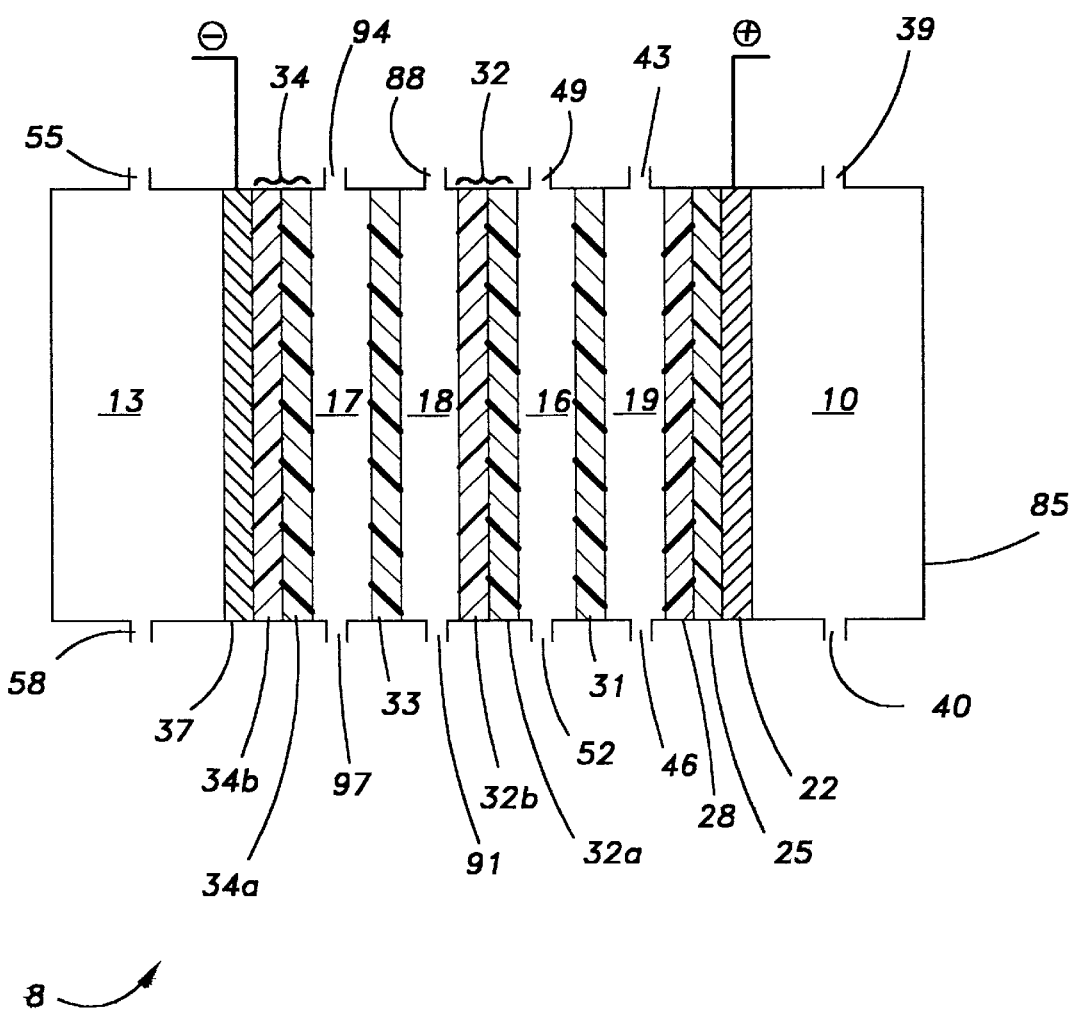
FIG. 2 is a schematic representation of an electrolytic cell similar to the electrolytic cell depicted in FIG. 1, but having two pairs of intermediate compartments.
Figure 3:
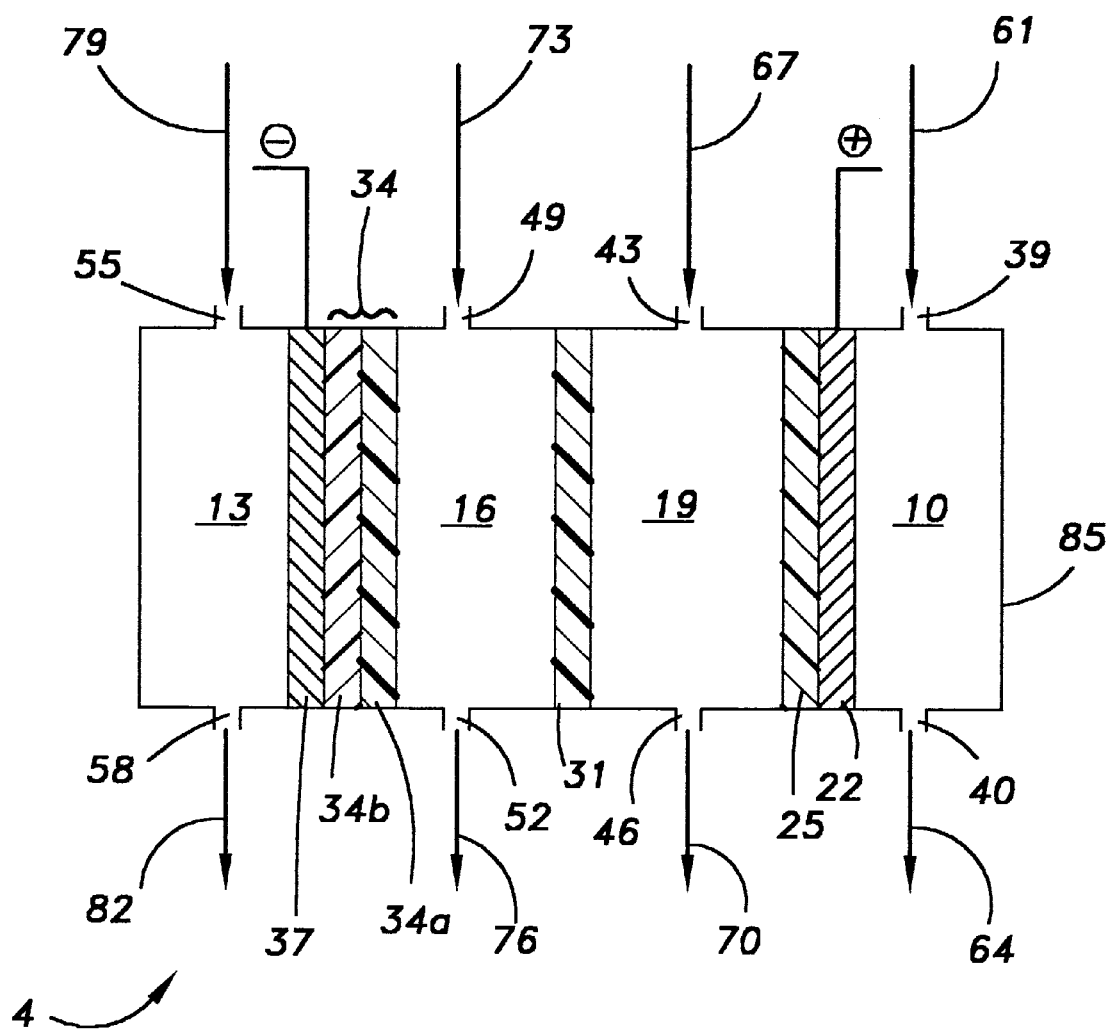
FIG. 3 is a schematic representation of an electrolytic cell similar to the electrolytic cell depicted in FIG. 1, but in which the hydraulic barrier is not present.

In the practice of the present invention, electrolytic cells, such as those represented in FIGS. 1 through 3, are provided for the conversion of amine hydrohalide to free amine. Referring now to FIG. 1, electrolytic cell 7 comprises a housing 85 having therein a catholyte compartment 13, an anode compartment 10, and one pair of intermediate compartments comprised of a first compartment 16 and a second compartment 19. The catholyte compartment 13 has an inlet 55 and an outlet 58, and contains therein a cathode assembly comprising a cathode 37 and a bipolar ion exchange membrane 34, which has a cation exchange side 34b and an anion exchange side 34a. The anode compartment 10 has an inlet 39 and an outlet 40, and contains therein an anode assembly comprising a hydrogen consuming gas diffusion anode 25 which is fixedly held between a current collecting electrode 22 and a hydraulic barrier 28. The first compartment 16 and the second compartment 19 of the pair of intermediate compartments are separated from each other by anion exchange membrane 31. Compartment 16 has an inlet 49, an outlet 52, and is separated from catholyte compartment 13 by the anion exchange side 34a of the bipolar ion exchange membrane 34, more particularly, the cathode assembly. Compartment 19 has an inlet 43, an outlet 46, and is separated from anode compartment 10 by hydraulic barrier 28, more particularly, the anode assembly.

FIG. 2 is a representation of an electrolytic cell 8 used in the practice of the method of the present invention. Electrolytic cell 8 is similar to electrolytic cell 7, but has a second pair of intermediate compartments 17 and 18. Compartment 17 is separated from compartment 18 by anion exchange membrane 33. Compartment 18 is separated from compartment 16 by intermediate bipolar ion exchange membrane 32. Intermediate bipolar ion exchange membrane 32 has a cation exchange side 32b which is closer to catholyte compartment 13, and an anion exchange side 32a which is closer to anode compartment 10. Compartment 17 and compartment 18 each have an inlet and an outlet, 94 and 97, 88 and 91, respectively.

When the electrolytic cell used in the practice of the present invention has more than one pair of intermediate compartments, each pair of intermediate compartments is separated from its adjacent pair of intermediate compartments by an intermediate bipolar ion exchange membrane. As used herein, the term "intermediate bipolar ion exchange membrane" refers to a bipolar ion exchange membrane that separates adjacent pairs of intermediate compartments and is other than the bipolar ion exchange membrane of the cathode assembly.

The electrolytic cells of FIGS. 1–3 may be assembled by any appropriate method as long as the basic structural arrangements of component parts, as depicted in FIGS. 1–3, are maintained. For example, the catholyte, anode and intermediate compartments may each be fabricated separately and then assembled by clamping or otherwise fastening the compartments together.

Housing 85 may be fabricated from any of the known conventional materials for electrolytic cells, or combinations of these known materials, that are preferably at least corrosion resistant to, and compatible with the materials being circulated through the catholyte, anode and intermediate compartments or formed in these compartments. Examples of materials from which housing 85 may be fabricated include, but are not limited to: metal, e.g., stainless steel, titanium, and nickel; plastics, e.g., poly(vinylidenefluoride), polytetrafluoroethylene which is sold under the trademark "TEFLON", and which is commercially available from E.I. du Pont de Nemours and Company of Wilmington, Del., USA, glass filled polytetrafluoroethylene, polypropylene, polyvinylchloride, chlorinated polyvinylchloride and high density polyethylene. Preferred materials from which housing 85 may be fabricated include, poly(vinylidenefluoride) and stainless steel.

If housing 85 is fabricated from an electrically conductive material, such as stainless steel, then appropriately positioned electrically nonconductive gaskets would typically also be present, as is known to those of ordinary skill in the art. For example, if the various compartments of the cell are prefabricated separately from stainless steel, such gaskets would typically be placed between those portions of the prefabricated compartments that would otherwise abut each other upon assemblage of the electrolytic cell. Such nonconductive gaskets may be fabricated from synthetic polymeric materials, e.g., copolymers of ethylene and propylene, and fluorinated polymers.

Cathode 37 and current collecting electrode 22 may each be fabricated from any appropriate material that is at least both corrosion resistant to the environments to which they are exposed and electrically conductive. In electrolytic cells 7, 8 and 4, it is also desirable that cathode 37 and current collecting electrode 22 be substantially rigid so as to provide support for, respectively, bipolar ion exchange membrane 34, and either hydrogen consuming gas diffusion anode 25 alone or the combination of hydrogen consuming gas diffusion anode 25 and hydraulic barrier 28. Materials from which cathode 37 and current collecting electrode 22 may be fabricated include, but are not limited to: graphite; platinum; titanium coated with platinum; titanium coated with an oxide of ruthenium; nickel; stainless steel; specialty steels including high alloy steels containing nickel, chromium and molybdenum, e.g., HASTELLOY® C-2000™ alloy and HASTELLOY® C-276™ alloy from Haynes International, Inc. While current collecting electrode 22 may be fabricated from stainless steel, it is preferred to use a more corrosion resistant material such as a high alloy steel, e.g., HASTELLOY® C-2000™ alloy. Cathode 37 and current collecting electrode 22 may each comprise a material selected from the group consisting of graphite, platinum, titanium coated with platinum, titanium coated with an oxide of ruthenium, nickel, stainless steel, high alloy steel and appropriate combinations of such materials.

Preferably both cathode 37 and current collecting electrode 22 have a perforated or mesh-like configuration. A perforated or mesh-like configuration provides for increased cathode and electrode surface area, and minimizes interference with the movement of ions across the bipolar ion exchange membrane, the hydrogen consuming gas diffusion barrier and also the hydraulic barrier.

The anion exchange membrane 31 used in the practice of the present invention may be prepared from any appropriate material that is permeable to and capable of transferring anions. Typically, such anion exchange membranes are comprised of commercially available organic polymers, often thermoplastic polymers, containing weakly basic pendant polar groups. The membranes may comprise polymers based on fluorocarbons, polystyrene, polypropylene, polybutadiene, polyisoprene, polyisobutylene, polyethylene and hydrogenated styrene/butadiene block copolymers. For example, one such representative anion exchange membrane comprises polystyrene which has dialkylamino groups that have been converted into quaternary ammonium ions covalently bonded to at least some of the benzene rings of the polystyrene backbone. It is preferable that the anion exchange membrane also be physically durable and stable towards exposure to acids, in particular hydrogen halides, e.g., hydrogen chloride.

A particular example of an anion exchange membrane used in the practice of the present invention is a copolymer of styrene and divinylbenzene which contains from 4 percent (%) to 16%, typically from 6% to 8% by weight of divinylbenzene and also quaternary ammonium groups as anion carriers. Such membranes are available commercially under the trade designation RAIPORE® from RAI Research Corporation, and TOSFLEX® from Tosoh Corporation. Other suitable membranes include, but are not limited to: NEOSEPTA® membranes from Tokyuama Soda; SELEMION membranes from Asahi Glass; IONAC MA 3148, MA 3236 and MA 3457 (based on a polymer of heterogeneous polyvinyl chloride substituted with quaternary ammonium groups) membranes from Ritter-Pfaulder Corporation. Particularly preferred anion exchange membranes are NEOSEPTA® ACM and NEOSEPTA® AHA-2 membranes, available commercially from Tokuyama Soda of Japan, which are described as being comprised of a copolymer of styrene and divinylbenzene having pendent quaternary ammonium groups.

In the practice of the method of the present invention, it is preferred that hydraulic barrier 28 prevent substantially the flow of liquid and hydrogen gas between compartment 19 and anode compartment 10, while also being permeable to hydrogen cations. The hydraulic barrier 28 may be, for example, a cation exchange membrane or a microporous film.

When hydraulic barrier 28 is a cation exchange membrane, it may be fabricated of any appropriate material that is also capable of transporting cations. Examples of classes of materials from which the cation exchange membrane may be fabricated include, but are not limited to, organic polymers, in particular synthetic organic polymers, and ceramics, e.g., beta-alumina. The use of synthetic organic polymers having pendent acidic groups is preferred, many of which are commercially available or can be made according to art-recognized methods. A preferred class of synthetic organic polymers are fluoropolymers, more preferably perfluoropolymers, and in particular copolymers comprised of two or more fluoromonomers or perfluoromonomers, having pendent acid groups, preferably pendent sulfonic acid groups.

When the cation exchange membrane is fabricated from fluorinated polymer(s) or copolymer(s), the pendent acid groups may include the following representative general formulas: $-CF_2CF(R)SO_3H$; and $-OCF_2CF_2CF_2SO_3H$, where R is a F, Cl, $CF_2Cl$, or a $C_1$ to $C_{10}$ perfluoroalkyl radical. The synthetic organic polymer of the cation exchange membrane may, for example, be a copolymer of ethylene and a perfluorinated monomer as represented by the following general formula, $CF_2=CFOCF_2CF(CF_3)OCF_2CF_2SO_3H$. These copolymers may have pendent sulfonyl fluoride groups ($-SO_2F$), rather than pendent sulfonic acid groups ($-SO_3H$). The sulfonyl fluoride groups ($-SO_2F$) can be reacted with potassium hydroxide to form $-SO_3K$ groups, which can then be reacted with an acid to form sulfonic acid groups $-SO_3H$.

Suitable cation exchange membranes comprised of copolymers of polytetrafluoroethylene and poly-sulfonyl fluoride vinyl ether-containing pendant sulfonic acid groups are offered by E.I. du Pont de Nemours and Company of Wilmington, Del. under the tradename "NAFION" (hereinafter referred to as NAFION®). In particular, NAFION® membranes containing pendant sulfonic acid groups include NAFION® 117, NAFION® 324 and NAFION® 417 membranes. The NAFION® 117 membrane is described as an unsupported membrane having an equivalent weight of 1100 grams per equivalent (g/eq), equivalent weight being here defined as that amount of resin required to neutralize one liter of a 1 Molar (M) sodium hydroxide solution. The NAFION® 324 and NAFION® 417 membranes are described as being supported on a fluorocarbon fabric. The NAFION® 417 membrane has an equivalent weight of 1100 g/eq. The NAFION® 324 membrane is described as having a two-layer structure comprised of: a 125 micrometer ($\mu$m) thick membrane having an equivalent weight of 1100 g/eq; and a 25 $\mu$m thick membrane having an equivalent weight of 1500 g/eq.

While the use of cation exchange membranes based on synthetic organic polymers are preferred as hydraulic barriers, it is within the scope of the practice of the method of the present invention to use other cation-transporting membranes which are not polymeric. For example, solid state proton conducting ceramics such as beta-alumina may be used. Examples of representative solid sate proton conductors are listed in columns 6 and 7 of U.S. Pat. No. 5,411,641, which are incorporated herein by reference.

Hydraulic barrier 28 may also be a microporous film. Microporous films are known and can be described as being heterogeneous structures having a solid phase containing voids. Microporous films useful in the present invention are preferably permeable to hydrogen cations and prevent substantially the flow of liquid and hydrogen gas between compartment 19 and anode compartment 10. Suitable microporous films may be comprised of synthetic organic polymers such as polypropylene or polysulfone. An example of a commercially available microporous film useful in the practice of the method of the present invention is available under the tradename CELGARD® from Hoechst-Celanese Corp.

Bipolar ion exchange membrane 34 and intermediate bipolar ion exchange membrane 32 each comprises an anion exchange side 34a and 32a, and a cation exchange side 34b and 32b, respectively. The anion and cation exchange sides of a bipolar ion exchange membrane are typically joined or otherwise laminated together, as is known to those of ordinary skill in the art. The anion and cation exchange sides are essentially the same as the free standing anion and cation exchange membranes previously described above. A more detailed description of bipolar ion exchange membranes useful in the present invention can be found in U.S. Pat. Nos. 4,024,043 and 4,116,889, the disclosure of which is incorporated herein in its entirety. Bipolar ion exchange membranes used in the practice of the present invention can be obtained commercially from Aqualytics, Division of The Graver Company.

When saturated with water, and under the passage of a direct current through electrolytic cell 7, it is believed that water is hydrolyzed at the interface between the anion and cation exchange sides of bipolar ion exchange membrane 34. The hydrolyzed water produces hydrogen cations and hydroxide anions. The hydrogen cations are transported across cation exchange side 34b towards cathode compartment 13. While the hydroxide anions are transported across anion exchange side 34a towards anode compartment 10.

Hydrogen consuming gas diffusion anode 25 may be fabricated from any suitable material or combinations of materials which provides an electrochemically active surface upon which hydrogen gas ($H_2$) can be converted to hydrogen cation ($H^+$), through which hydrogen cations may diffuse, and which is also semihydrophobic. By semihydrophobic is meant that an aqueous liquid can penetrate the anode without flooding it, i.e., without preventing the electrochemical conversion of hydrogen gas to hydrogen cation. The electrochemical activity is typically provided by a catalytic material. Examples of suitable catalytic materials include, but are not limited to, platinum, ruthenium, osmium, rhenium, rhodium, iridium, palladium, tungsten carbide, gold, titanium, zirconium, alloys of these with non-noble metals and appropriate combinations thereof.

The hydrogen consuming gas diffusion anode 25 used in the practice of the present invention is preferably comprised of platinum, e.g., platinum supported on carbon, preferably hydrophilic carbon, or finely powdered platinum (platinum black), which has been dispersed in a polymer matrix. The polymer matrix may comprise polymers of, for example, fluorinated and perfluorinated monomers. A preferred polymer in which platinum supported on hydrophilic carbon may be dispersed is polytetrafluoroethylene. The hydrogen consuming gas diffusion anode 25 may comprise from 0.1 milligrams platinum per square centimeter of the surface area of the hydrogen consuming gas diffusion anode (mg/cm$^2$) to 15 mg/cm$^2$, preferably from 0.5 mg/cm$^2$ to 10 mg/cm$^2$, and more preferably from 0.5 mg/cm$^2$ to 6 mg/cm$^2$.

The method of the present invention may also be practiced using an electrolytic cell in which the anode assembly comprises hydrogen consuming gas diffusion anode 25 and current collecting electrode 22, wherein compartment 19 is separated from anode compartment 10 by hydrogen consuming gas diffusion anode 25. Such a cell is represented as electrolytic cell 4 in FIG. 3. In addition to the characteristics previously recited, it is desirable that the hydrogen consuming gas diffusion anode 25 of electrolytic cell 4 also prevent substantially the flow of hydrogen gas and aqueous liquid between compartment 19 and anode compartment 10.

Within anode compartment 10 of electrolytic cells 7 and 4, the method by which the anode assembly is held together may be achieved by any appropriate means. Such methods include, but are not limited to: maintaining a higher internal pressure within compartment 16 and compartment 19 relative to anode compartment 10 and catholyte compartment 13; the method of clamping the components, 28, 25 and 22, or 25 and 22 together; providing a biasing element within, at least, each of compartments 16 and 19, e.g., separate electrically nonconductive plastic springs, not shown, can be placed within each of the intermediate compartments such that the spring placed within compartment 16 is in biased contact with bipolar ion exchange membrane 34 and anion exchange membrane 31, and the spring placed within compartment 19 is in biased contact with anion exchange membrane 31 and either hydrogen consuming gas diffusion anode 25 or hydraulic barrier 28; and combinations of these methods.

In one embodiment of the present invention hydrogen consuming gas diffusion anode 25 is hot-pressed onto one side of hydraulic barrier 28. In another embodiment of the present invention, hydrogen consuming gas diffusion anode 25 is simply placed between hydraulic barrier 28 and current collecting electrode 22 prior to assembly of the electrolytic cell. In yet another embodiment of the present invention, carbon cloth or carbon paper, not shown, is placed between hydrogen consuming gas diffusion anode 25 and current collecting electrode 22 to provide additional support to the hydrogen consuming gas diffusion anode. The carbon cloth and carbon paper are both preferably semihydrophobic, e.g., treated with TEFLON® polytetrafluoroethylene prior to use. Optionally the carbon cloth and carbon paper may also be impregnated with a catalytic material, such as platinum.

Ensuring that electrical contact exists between anode 25 and electrode 22 is important in the practice of the present invention. This is the case when the anode assembly is comprised of either (a) hydrogen consuming gas diffusion anode 25 fixedly held between hydraulic barrier 28 and current collecting electrode 22, or (b) hydrogen consuming gas diffusion anode 25 and current collecting electrode 22. In one embodiment of the present invention, electrical contact is maintained between hydrogen consuming gas diffusion anode 25 and current collecting electrode 22 by ensuring that a positive internal pressure difference exists between at least compartment 19 and anode compartment 10. By positive internal pressure difference is here meant that compartment 19 has an internal pressure greater than that of anode compartment 10. In this case the positive internal pressure difference value is determined by subtracting the internal pressure of anode compartment 10 from that of compartment 19. It is preferred that the internal pressure of compartment 16 be equivalent to that of compartment 19 and either equal to or greater than that of catholyte compartment 13.

The upper limit of the positive internal pressure difference between the intermediate compartments and each of catholyte compartment 13 and anode compartment 10 will depend on a number of factors including, for example, the maximum pressure that the bipolar ion exchange membrane, the anion exchange membrane, and either the hydraulic barrier or the hydrogen consuming gas diffusion anode can endure before they burst or rupture. In the practice of the present invention, the positive internal pressure difference between the intermediate compartments and each of the catholyte and anode compartments typically has a minimum value of at least 0.07 Kilograms per square centimeter ($Kg/cm^2$) (1 pound per square inch (psi)), preferably at least 0.14 $Kg/cm^2$ (2 psi), and more preferably at least 0.21 $Kg/cm^2$ (3 psi). The positive internal pressure difference between the intermediate compartments and each of the catholyte and anode compartments typically has a maximum value of less than 1.40 $Kg/cm^2$ (20 psi), preferably less than 0.70 $Kg/cm^2$ (10 psi), and more preferably less than 0.49 $Kg/cm^2$ (7 psi). In the practice of the method of the present invention, the positive internal pressure difference between the intermediate compartments and each of the catholyte and anode compartments may range between any combination of these minimum and maximum values, inclusive of the recited values.

The present invention relates to a method of converting amine hydrohalide into free amine. As used herein, the term "halide" is meant to include chloride, bromide and iodide. Classes of free amines that may be prepared from the corresponding amine hydrohalides according to the method of the present invention include, but are not limited to: ammonia; mono alkyl, e.g., $C_1$–$C_{12}$ alkyl, amines, di- and tri-substituted alkyl, e.g., $C_1$–$C_{12}$ alkyl, amines, in which the alkyl groups may be the same or different, saturated or unsaturated, examples of saturated alkyl groups include, but are not limited to, methyl, ethyl, isopropyl, n-butyl, tertbutyl, amyl and dodecyl, examples of unsaturated alkyl groups, include, but are not limited to, allyl and methallyl; one or more amines belonging to the family of ethyleneamines, including, ethylenediamine (EDA), diethylenetriamine (DETA), triethylenetetramine (TETA), tetraethylenepentamine (TEPA), pentaethylenehexamine (PEHA), piperazine (DEDA), and 2-amino-1-ethylpiperazine; alkyl, e.g., $C_1$–$C_2$ alkyl, ethylenediamines, e.g., N-ethylethylenediamine, N,N-dimethylethylenediamine, N,N'-dimethylethylenediamine, N,N-diethylethylenediamine, N,N'-diethylethylenediamine, N,N-dimethyl-N'-ethylethylenediamine, and N,N,N',N'-tetramethylethylenediamine; propylenediamines, e.g., 1,2-propylenediamine, and 1,3-propylenediamine; alkyl, e.g., $C_1$–$C_3$ alkyl, propylenediamines, e.g., N-methyl-1,3-propylenediamine; alkanolamines, e.g., mono-, di- and tri (2-hydroxyethyl)amine; alkylamino alkanols, e.g., $C_1$–$C_6$ alkylamino $C_1$–$C_{12}$ alkanols, e.g., 2-(ethylamino)ethanol, and 2-(diethylamino)ethanol; $C_5$–$C_7$ cycloaliphatic amines, e.g., cyclohexylamine, N-methylcyclohexylamine, and 1,4-diazobicyclo[2.2.2]octane; and aromatic amines, e.g., aniline, N-ethylaniline, and N,N-diethylaniline.

As used herein, the term "ethyleneamine" is meant to refer to one or more amines belonging to the family of ethyleneamines as previously recited. In a preferred embodiment of the present invention, the amine hydrohalide is an amine hydrochloride, and the amine of the amine of the amine hydrochloride is selected from the group consisting of ammonia, monoalkylamines, dialkylamines, trialkylamines, ethyleneamines, alkyl ethylenediamines, propylenediamines, alkyl propylenediamines, monoalkanolamines, dialkanolamines, trialkanolamines, cycloaliphatic amines, aromatic amines and mixtures of such amines, as described previously. In a particularly preferred embodiment of the present invention, the amine of the amine hydrochloride is an "ethyleneamine" and is selected from the group consisting of ethylenediamine, diethylenetriamine, triethylenetetramine, tetraethylenepentamine, pentaethylenehexamine, piperazine, 1-(2-aminoethyl)piperazine and mixtures of such ethyleneamines.

The operation of electrolytic cells 7 and 4 of FIGS. 1 and 3 will now be described as they relate to preferred embodiments of the process of the present invention. A first aqueous conductive electrolyte solution is circulated through catholyte compartment 13 by forwarding the solution from a source of first aqueous conductive electrolyte solution, e.g., a temperature controlled reservoir not shown, through a suitable conduit (shown by line 79); introducing the first solution into catholyte compartment 13 through inlet 55; withdrawing a process stream comprising the first aqueous conductive electrolyte solution from compartment 13 through outlet 58; and forwarding that process stream by a suitable conduit (shown by line 82) to the source of first electrolyte solution, e.g., a reservoir not shown.

Similarly and simultaneously with the circulation of the first aqueous conductive electrolyte solution through catholyte compartment 13, a second aqueous conductive electrolyte solution is circulated through compartment 19 by forwarding the solution from a source of second aqueous conductive electrolyte solution, e.g., a temperature controlled reservoir not shown, through a suitable conduit (shown by line 67); introducing the second solution into compartment 19 through inlet 43; withdrawing a process stream comprising the second aqueous conductive electrolyte solution from compartment 19 through outlet 46; and forwarding that process stream by a suitable conduit (shown by line 70) to the source of second electrolyte solution, e.g., a reservoir not shown.

The first and second aqueous conductive electrolyte solutions circulated through the catholyte and second compartments respectively, are capable of conducting an electric current. It is contemplated that the first and second aqueous conductive electrolyte solutions can be circulated from the same temperature controlled reservoir, not shown.

The first and second aqueous conductive electrolyte solutions may have present therein hydrogen halide, e.g., hydrogen chloride, and/or an alkali metal halide, e.g., sodium chloride, the halide being the same as that of the amine hydrohalide. In a preferred embodiment of the present invention, the first and second aqueous conductive electrolyte solutions are each comprised of an aqueous solution of hydrogen chloride, wherein the hydrogen chloride is present in an amount of at least 1% by weight, preferably at least 5% by weight, and more preferably at least 10% by weight, based on the total weight of the aqueous conductive electrolyte solution. The hydrogen chloride is also present in the first and second aqueous conductive electrolyte solutions in an amount less than 25% by weight, preferably less than 20% by weight, and more preferably less than 15% by weight, based on the total weight of the aqueous conductive electrolyte solution. The amount of hydrogen chloride present may range between any of these amounts, inclusive of the recited amounts.

The temperature at which the first and second aqueous conductive electrolyte solutions are maintained depends on, for example, their respective boiling points and the operating temperature limits of anion exchange membrane 31 and either hydrogen consuming gas diffusion anode 25 or hydraulic barrier 28. In the practice of the present invention, the first and second aqueous conductive electrolyte solutions are each typically maintained at a temperature of at least 25° C., preferably at least 30° C., and more preferably at least 40° C. The first and second aqueous conductive electrolyte solutions are also typically maintained at a temperature of less than 70° C., preferably less than 65° C., and more preferably less than 60° C. The temperature at which the first and second aqueous conductive electrolyte solutions are each maintained may range between any combination of these temperatures, inclusive of the recited temperatures.

Contemporaneously and in a manner similar to the circulation of the first and second aqueous conductive electrolyte solutions through their respective compartments, an aqueous solution of amine hydrohalide is circulated through compartment 16 by forwarding amine hydrohalide solution from of a source of amine hydrohalide, e.g., a temperature controlled reservoir not shown, through a suitable conduit (shown by line 73); introducing the amine hydrohalide solution into compartment 16 through inlet 49; withdrawing a process stream comprising free amine and amine hydrohalide from compartment 16 through outlet 52; and forwarding that process stream by a suitable conduit (shown by line 76) to the source of amine hydrohalide, e.g., a reservoir not shown.

The temperature at which the aqueous solution of amine hydrohalide is maintained will depend on, for example, its boiling point and the operating temperature limits of anion exchange membrane 31 and bipolar ion exchange membrane 34. In the practice of the present invention, the aqueous solution of amine hydrohalide is typically maintained at a minimum temperature of at least 25° C., preferably at least 30° C., and more preferably at least 40° C. The aqueous solution of amine hydrohalide is also typically maintained at a maximum temperature of less than 70° C., preferably less than 65° C., and more preferably less than 60° C. The temperature at which the aqueous solution of amine hydrohalide is maintained may range between any combination of these minimum and maximum temperature values, inclusive of the recited values.

The aqueous solution of amine hydrohalide typically contains amine hydrohalide present in an amount of at least 5% by weight, preferably at least 10% by weight, and more preferably at least 25% by weight, based on the total weight of the aqueous solution of amine hydrohalide. The aqueous solution of amine hydrohalide also typically contains amine hydrohalide present in an amount of less than 50% by weight, preferably less than 40% by weight, and more preferably less than 35% by weight, based on the total weight of the aqueous solution of amine hydrohalide. The amount of amine hydrohalide present in the aqueous solution of amine hydrohalide may range between any combination of these amounts, inclusive of the recited amounts.

Concurrently and in a manner similar to the circulation of the first and second aqueous conductive electrolyte solutions and the aqueous solution of amine hydrohalide through their respective compartments, hydrogen gas is circulated through anode compartment 10 by forwarding hydrogen gas from a source of hydrogen, e.g., a reservoir not shown, through a suitable conduit or transfer line (shown by line 61); introducing such hydrogen gas into anode compartment 10 through inlet 39; withdrawing hydrogen gas from anode compartment 10 through outlet 40; and forwarding withdrawn hydrogen gas by a suitable conduit or transfer line (shown by line 64) to the source of hydrogen, e.g., a reservoir not shown. Other gas(es) may be present with the hydrogen gas circulated through anode compartment 10, e.g., nitrogen, as long as such other gas(es) do not adversely affect the operation of the electrolytic cell. In particular, it is preferred that the hydrogen gas-containing stream be substantially free of carbon monoxide (CO) as carbon monoxide can poison or otherwise degrade the gas diffusion hydrogen gas anode 25.

Electrolytic cells 7 and 4 may be operated at a current density of at least 0.05 Kiloamperes per square meter of electrode surface available for electrochemical reaction (Kamps/m²), preferably at least 0.1 Kamps/m², and more preferably at least 0.2 Kamps/m². The current density also may be not more than 10 Kamps/m², preferably not more than 7 Kamps/m², and more preferably not more than 6 Kamps/m². In the practice of the present invention, the current density may range between any combination of these values, inclusive of the recited values. The surface area of the electrode being here calculated from its perimeter dimensions alone.

While not meaning to be bound by any theory, it is believed from the evidence at hand that the current passing through electrolytic cells 7 and 4 results in the following chemical and electrochemical reactions. The electrochemical and chemical reactions believed to occur within catholyte compartment 13 may be represented by the following General Scheme I:

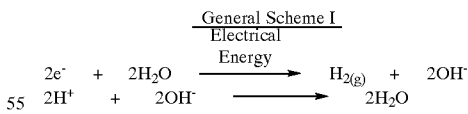

wherein e⁻ represents an electron, OH⁻ represents a hydroxide anion, and H⁺ represents a hydrogen cation. The hydrogen cation H⁺, formed from the hydrolysis of water at the interface of cation exchange side 34b and anion exchange side 34a of bipolar ion exchange membrane 34, is transported across cation exchange side 34b of membrane 34 and passes into catholyte compartment 13. The electrons consumed, as shown in General Scheme I, are provided by cathode 37. Hydrogen gas generated within catholyte compartment 13 is forwarded with the first aqueous conductive electrolyte process stream through a conduit (shown by line 82) from which hydrogen gas may be removed at a convenient point, not shown. Alternatively, the hydrogen gas removed from the conduit represented by line 82 may be forwarded to a hydrogen gas reservoir, not shown, for recycle into anode compartment 10 by means of conduits not shown.

Within anode compartment 10, the following electrochemical reaction is believed to occur as represented by General Scheme II:

$$H_{2(g)} \xrightarrow{\text{Electrical Energy}} 2H^+ + 2e^-$$

General Scheme II

Hydrogen cations ($H^+$) produced within and/or on the surface of anode 25 move across hydraulic barrier 28 and pass into compartment 19, in the case of electrolytic cell 7 of FIG. 1. In the case of electrolytic cell 4 of FIG. 3, the hydrogen cations diffuse directly through hydrogen consuming gas diffusion anode 25 into compartment 19. The electrons generated, as shown in General Scheme II, are transferred by electrical contact from hydrogen consuming gas diffusion anode 25 to current collecting electrode 22.

Within compartment 16 the following chemical reaction is believed to occur as represented by General Scheme III:

$$BH^+X^- + OH^- \rightarrow B + H_2O + X^-$$  General Scheme III wherein $BH^+X^-$ represents an amine hydrohalide, $X^-$ represents a halide anion, and B represents free amine. The hydroxide anion ($OH^-$), formed from the hydrolysis of water at the interface of cation exchange side 34b and anion exchange side 34a of bipolar ion exchange membrane 34, is transported across anion exchange side 34a into compartment 16. The halide anion $X^-$ is selectively transported across anion exchange membrane 31 into compartment 19, and therein forms aqueous hydrogen halide with the hydrogen cation transported across hydraulic barrier 28 or hydrogen consuming gas diffusion anode 25.

The practice of the method of the present invention includes the step of removing an aqueous solution comprising free amine from compartment 16, and forwarding this process stream through conduit 76. The process stream withdrawn from compartment 16 will contain a higher amount of free amine than the process stream entering compartment 16.

When the concentration of free amine in the process stream circulating through compartment 16 reaches a desired level, the free amine is recovered from that stream. The aqueous solution from which the free amine is recovered will typically contain an amount of free amine that is at least 50 percent greater than that of the aqueous solution of amine hydrohalide initially charged to compartment 16. Of the total mole equivalents of amine hydrohalide initially present in the aqueous solution of amine hydrohalide circulated through compartment 16, at least 50%, preferably at least 80%, and more preferably at least 95% of these equivalents are converted to free amine in accordance with the practice of the method of the present invention.

While a batch process has been described, a continuous process for converting the amine hydrohalide to free amine is contemplated. For example, a side stream of the circulating aqueous stream of amine hydrohalide can be removed at a convenient point, not shown, to make the process a continuous or semi-continuous process.

In one contemplated embodiment of the present invention, electrolytic cells 7 or 4 are operated until 95% to 99.5%, and preferably 98% to 99.5% of the total mole equivalents of amine hydrohalide initially present in the aqueous solution of amine hydrohalide introduced into compartment 16 are converted to free amine. To convert the remaining, e.g., 0.5% to 5%, equivalents of unconverted amine hydrohalide to free amine, the aqueous solution comprising free amine removed from compartment 16 may be treated with a small amount of alkali metal hydroxide, e.g., sodium hydroxide, followed by separation of the resulting alkali metal halide salt, e.g., sodium chloride.

In a modification of the above embodiment, the remaining, e.g., 0.5% to 5%, mole equivalents of unconverted amine hydrohalide are converted to free amine by passing the aqueous solution comprising free amine removed from compartment 16 through an anion exchange resin, which is contained in one or more anion exchange columns. For example, the removed aqueous solution comprising free amine containing from for example 0.5% to 5% equivalents of unconverted amine hydrohalide, based on the total equivalents of amine hydrohalide initially present in the aqueous solution of amine hydrohalide, is passed through an anion exchange column or a series of anion exchange columns containing anion exchange resins, which exchange hydroxide anions ($OH^-$) for halide anions ($X^-$). The hydroxide anions released from the column(s) serve to convert the amine cation ($BH^+$) to free amine (B) and water.

Ion exchange columns useful in the aforedescribed finishing process, are well known and typically are filled with a solid sorbant material comprised of a porous water insoluble synthetic organic polymer having acidic or basic groups, along the polymer backbone (ion exchange resin). Cation exchange resins have acidic groups, while anion exchange resins have basic groups along the polymer backbone. Examples of suitable organic polymers from which the sorbant material may be comprised include, but are not limited to, phenolic based polymers, styrene based polymers and acrylic based polymers. A general illustrative example of an anion exchange resin is polystyrene having either quaternary ammonium groups or tertiary amine groups covalently bonded to at least some of the benzene rings of the polystyrene backbone. An example of an anion exchange resin useful in the practice of the present invention is commercially available under the tradename AMBERJET® 4400 OH, from Rohm and Hass Company.

During operation of electrolytic cells 7 and 4, the concentration of hydrogen halide, e.g., hydrogen chloride, within the second aqueous conductive electrolyte solution in compartment 19 will increase with each pass of the circulating solution through compartment 19. The aqueous hydrogen halide process stream removed from compartment 19 will contain a higher amount of hydrogen halide than the process stream entering compartment 19 by means of conduit 67.

If the concentration of hydrogen halide within compartment 19 becomes too high, e.g., in excess of 25% by weight in the case of hydrogen chloride, based on the total weight of the second aqueous conductive electrolyte solution, the operating efficiency of the electrolytic cell 7 will likely begin to degrade. Examples of degraded operating efficiency include, higher required operating cell potentials and reduced current efficiency resulting from back migration of protons and halide anions across the various ion exchange membranes, hydraulic barrier 28 and hydrogen consuming gas diffusion anode 25.

Two further and separate embodiments of the present invention are directed to the step of maintaining the hydrogen halide concentration of the second aqueous conductive electrolyte solution circulated through compartment 19 below 25% by weight, preferably below 20% by weight, and more preferably below 15% by weight, based on the total weight of the second aqueous conductive electrolyte solution.

In the first of these two separate embodiments, the concentration of hydrogen halide within the second aqueous conductive electrolyte solution is maintained below 25% by weight by introducing into compartment 19 an aqueous stream selected from the group consisting of water, aqueous alkali metal hydroxide, e.g., aqueous sodium hydroxide, and a mixture of aqueous alkali metal hydroxide and alkali metal halide, e.g., a mixture of aqueous sodium hydroxide and sodium chloride. More specifically, this aqueous reagent stream is introduced into conduit 67 at a point not shown and is forwarded along with the circulating second aqueous conductive electrolyte solution into compartment 19 through inlet 43 by means of said conduit 67.

Within compartment 19, the introduced alkali metal hydroxide can combine with the hydrogen halide, e.g. hydrogen chloride, to form water and alkali halide, e.g., sodium chloride, or the introduced water will dilute the second aqueous conductive electrolyte solution. The resultant solution exits compartment 19 through outlet 46 and is forwarded through conduit 70 to, for example, the reservoir from which the second aqueous electrolyte solution is circulated, not shown. The amount of water/reagent introduced into compartment 19 can be controlled automatically, for example, through the use of a metering device having a pH feed-back control loop, not shown. Depending on the volume of aqueous process stream added to compartment 19, the volume capacity of the reservoir from which the second aqueous electrolyte solution is circulated, not shown, may be exceeded, requiring that some of the combined added aqueous stream and second aqueous electrolyte solution be removed, e.g., as a bleed stream, from the circulating solution at a convenient point through a conduit, not shown.

In the second of these two separate embodiments, the concentration of hydrogen halide within the second aqueous conductive electrolyte solution is maintained below 25% by weight by: distilling the second aqueous conductive electrolyte solution removed from compartment 19 in a distillation column not shown; removing concentrated hydrogen halide distillate product and bottoms product from the distillation column; and either (a) returning the bottoms to compartment 19 or (b) introducing an aqueous stream selected from the group consisting of water and an aqueous conductive electrolyte solution having a concentration of hydrogen halide of less than 25% by weight, preferably less than 20% by weight, and more preferably less than 15% by weight, based on the total weight of the aqueous conductive electrolyte solution, into compartment 19, by means of conduits and/or transfer lines not shown. The bottoms product may optionally be run through a heat exchanger, not shown, prior to the optional return of said bottoms product to said compartment 19.

The operation of a distillation column as described above results in a reduction in volume of the second aqueous conductive electrolyte solution circulating through compartment 19. As a result, make-up water or a make-up aqueous conductive electrolyte solution having a concentration of hydrogen halide of less than 25% by weight, based on the total weight of the make-up aqueous conductive electrolyte solution, is introduced into compartment 19 to replenish the reduced volume. This can be done by introducing make-up water or make-up aqueous conductive electrolyte solution having a concentration of hydrogen halide of less than 25% by weight, based on the total weight of the make-up aqueous conductive electrolyte solution, into conduit 67 at a convenient point not shown.

Distillation columns are well known and are typically operated under conditions that result in favorable or desirable vapor-liquid equilibria. The temperature and the pressure under which a distillation column is operated can be adjusted together to shift the azeotrope point of the mixture being distilled such that a desired concentration of one or more of the components of the mixture may be retrieved. Depending on the nature of the mixture which is to be distilled, the distillation column can be of the plate type, e.g., crossflow plate or counterflow plate, or packed type.

In the practice of the present invention, when the hydrogen halide is hydrogen chloride, the hydrogen halide distillation column, not shown, is operated under the following representative conditions: a pressure of from 7.03 Kg/cm$^2$ (100 psi) to 8.44 Kg/cm$^2$ (120 psi); a feed temperature of 24° C. to 35° C.; an overhead temperature of from 32° C. to 43° C.; and a bottoms temperature of from 149° C. to 177° C. Under these conditions the concentrated hydrogen chloride distillate product exiting the distillation column has a concentration of hydrogen chloride of from 99% by weight to 99.98% by weight, based on the total weight of concentrated hydrogen chloride distillate. The bottoms product exiting the distillation column has a hydrogen chloride concentration of from 12% to 15% by weight, based on the total weight of the bottoms. The hydrogen halide distillation column is preferably of the packed type, which uses acid corrosion resistant packing materials, e.g., packing materials based on silicon carbide, and is constructed of sufficiently acid corrosion resistant materials, e.g., titanium, tantalum, stainless steel and TEFLON® polytetrafluoroethylene lined stainless steel.

While FIGS. 1–3 depict singular representations of electrolytic cells, it should be understood that the scope of the present invention is also inclusive of the utilization of a plurality of such cells. The present invention may be practiced using a plurality of cells, e.g., electrolytic cells 7 or 4, either in series or parallel. In one embodiment, a plurality of cells, not shown, e.g., cell 7, are utilized in series, wherein the outlets 58, 52, 46 and 40 of each preceding cell are in respective communication with the inlets 55, 49, 43 and 39 of each succeeding cell by means of additional conduits, not shown.

In another embodiment of the present invention, a plurality of cells, not shown, e.g., cell 7, are utilized in parallel, wherein, for example, inlet 55 and outlet 58 of catholyte compartment 13 of each cell are in common closed loop communication with a common reservoir, not shown, by means of conduits and manifolds, not shown. Accordingly, the inlets and outlets of compartment 16, compartment 19 and anode compartment 10 of each cell are in common closed loop communication with their respective reservoirs, not shown, by means of additional conduits and manifolds, not shown.

The present invention has been described with reference to specific details of particular embodiments thereof. It is not intended that such details be regarded as limitations upon the scope of the invention except insofar as and to the extent that they are included in the accompanying claims.

We claim:

1. A method of converting amine hydrohalide into free amine comprising:

(a) providing an electrolytic cell having a catholyte compartment containing a cathode assembly; an anode compartment containing an anode assembly; and at least one pair of intermediate compartments separating said catholyte and anode compartments, said pair of intermediate compartments having a first compartment and a second compartment;

(b) introducing a first aqueous conductive electrolyte solution into said catholyte compartment;

(c) introducing hydrogen gas into said anode compartment;

(d) introducing an aqueous solution of amine hydrohalide into said first compartment of said pair of intermediate compartments;

(e) introducing a second aqueous conductive electrolyte solution into said second compartment of said pair of intermediate compartments;

(f) passing direct current through said electrolytic cell; and (g) removing an aqueous solution comprising free amine from said first compartment of said intermediate compartments; said cathode assembly comprising a cathode and a bipolar ion exchange membrane, said bipolar ion exchange membrane having a cation exchange side and an anion exchange side; said anode assembly comprising a hydrogen consuming gas diffusion anode and a current collecting electrode; said first compartment and said second compartment of said pair of intermediate compartments being separated from each other by an anion exchange membrane, said first compartment being defined by said anion exchange side of said bipolar ion exchange membrane and said anion exchange membrane, said second compartment being defined by said anion exchange membrane and said hydrogen consuming gas diffusion anode; provided that when said electrolytic cell has more than one pair of intermediate compartments, each pair of intermediate compartments is separated from its adjacent pair of intermediate compartments by an intermediate bipolar ion exchange membrane having a cation exchange side located on the side of said intermediate bipolar ion exchange membrane that is closer to said catholyte compartment and an anion exchange side located on the side of said intermediate bipolar ion exchange membrane that is closer to said anode compartment.

2. The method of claim 1 wherein said anode assembly further comprises a hydraulic barrier, said hydrogen consuming gas diffusion anode being fixedly held between said hydraulic barrier and said current collecting electrode, and said second compartment of said pair of intermediate compartments is separated from said anode compartment by said hydraulic barrier.

3. The method of claim 2 wherein the amine hydrohalide is an amine hydrochloride.

4. The method of claim 3 wherein the amine of the amine hydrochloride is selected from the group consisting of ammonia, monoalkylamines, dialkylamines, trialkylamines, ethyleneamines, alkyl ethylenediamines, propylenediamines, alkyl propylenediamines, monoalkanolamines, dialkanolamines, trialkanolamines, cycloaliphatic amines, aromatic amines and mixtures thereof.

5. The method of claim 4 wherein the amine of the amine hydrochloride is ethyleneamine and is selected from the group consisting of ethylenediamine, diethylenetriamine, triethylenetetramine, tetraethylenepentamine, pentaethylenehexamine, piperazine, 1-(2-aminoethyl) piperazine and mixtures thereof.

6. The method of claim 2 wherein said first and second aqueous conductive electrolyte solutions each comprises a hydrogen halide aqueous solution having a concentration of from 1% by weight to 25% by weight hydrogen halide, based on the total weight of each of said first and second aqueous conductive electrolyte solutions.

7. The method of claim 2 wherein said second aqueous conductive electrolyte solution comprises hydrogen halide, and said method further comprises maintaining the hydrogen halide concentration of said second aqueous conductive electrolyte solution introduced into said second compartment below 25% by weight, based on the total weight of said second aqueous conductive electrolyte solution.

8. The method of claim 7 wherein the concentration of said hydrogen halide in said second aqueous conductive electrolyte solution is maintained below 25% by weight by introducing an aqueous stream selected from a member of the group consisting of water, aqueous alkali metal hydroxide, and a mixture of aqueous alkali metal hydroxide and alkali metal halide into said second compartment.

9. The method of claim 7 wherein the concentration of said hydrogen halide of said second aqueous conductive electrolyte solution is maintained below 25% by weight by distilling second aqueous conductive electrolyte solution removed from said second compartment to produce a concentrated hydrogen halide distillate product and bottoms product; and either (a) returning the bottoms product to said second compartment or (b) introducing an aqueous stream selected from the group consisting of water and an aqueous conductive electrolyte solution having a concentration of hydrogen halide of less than 25% by weight, based on the total weight of said aqueous conductive electrolyte solution, into said second compartment.

10. The method of claim 2 wherein a positive internal pressure difference of from 0.07 Kg/cm$^2$ to 1.40 Kg/cm$^2$ exists between said pair of intermediate compartments and each of said catholyte compartment and anode compartment.

11. The method of claim 2 wherein said hydrogen consuming gas diffusion anode comprises platinum supported on carbon dispersed in polytetrafluoroethylene.

12. The method of claim 11 wherein said cathode and said current collecting electrode each comprises a material selected from the group consisting of graphite, platinum, titanium coated with platinum, titanium coated with an oxide of ruthenium, nickel, stainless steel, high alloy steel and appropriate combinations thereof.

13. The method of claim 12 wherein said anion exchange membrane and said anion exchange side of said bipolar exchange membrane each comprises a copolymer of styrene and divinylbenzene having pendent quaternary ammonium groups, said hydraulic barrier is a cation exchange membrane, and said cation exchange side of said bipolar exchange membrane and said hydraulic barrier each comprises a perfluoropolymer having pendent sulfonic acid groups.

14. The method of claim 2 further comprising passing aqueous solution comprising free amine removed from said first compartment through an anion exchange resin.

15. The method of claim 2 wherein said hydrogen consuming gas diffusion anode comprises platinum supported on carbon dispersed in polytetrafluoroethylene; said anion exchange membrane and said anion exchange side of said bipolar exchange membrane each comprises a copolymer of styrene and divinylbenzene having pendent quaternary ammonium groups; said hydraulic barrier is a cation exchange membrane; said cation exchange side of said bipolar exchange membrane and said hydraulic barrier each comprises a perfluoropolymer having pendent sulfonic acid groups.

16. The method of claim 15 wherein the amine of the amine hydrohalide is ethyleneamine and is selected from the group consisting of ethylenediamine, diethylenetriamine, triethylenetetramine, tetraethylenepentamine, pentaethylenehexamine, piperazine, 1-(2-aminoethyl) piperazine and mixtures thereof.

17. The method of claim 16 wherein said cathode and said current collecting electrode each comprises a material selected from the group consisting of graphite, platinum, titanium coated with platinum, titanium coated with an oxide of ruthenium, nickel, stainless steel, high alloy steel and appropriate combinations thereof; and a positive internal pressure difference of from 0.07 Kg/cm$^2$ to 1.40 Kg/cm$^2$ exists between said pair of intermediate compartments and each of said catholyte compartment and anode compartment.

18. The method of claim 17 wherein said second aqueous conductive electrolyte solution comprises hydrogen chloride, and said method further comprises maintaining the hydrogen chloride concentration of said second aqueous conductive electrolyte solution introduced into said second compartment below 25% by weight, based on the total weight of said second aqueous conductive electrolyte solution.

19. The method of claim 18 wherein the concentration of said hydrogen chloride of said second aqueous conductive electrolyte solution is maintained below 25% by weight by introducing an aqueous stream selected from a member of the group consisting of water, aqueous alkali metal hydroxide, and a mixture of aqueous alkali metal hydroxide and alkali metal halide into said second compartment.

20. The method of claim 18 wherein the concentration of said hydrogen chloride of said second aqueous conductive electrolyte solution is maintained below 25% by weight by distilling second aqueous conductive electrolyte solution removed from said second compartment to produce a concentrated hydrogen halide distillate product and bottoms product; and either (a) returning the bottoms product to said second compartment or (b) introducing an aqueous stream selected from the group consisting of water and an aqueous conductive electrolyte solution having a concentration of hydrogen halide of less than 25% by weight, based on the total weight of said aqueous conductive electrolyte solution, into said second compartment.

21. The method of claim 15 further comprising passing aqueous solution comprising free amine removed from said first compartment through an anion exchange resin.

22. An electrolytic cell comprising: a catholyte compartment containing a cathode assembly; an anode compartment containing an anode assembly; and at least one pair of intermediate compartments separating said catholyte and anode compartments, said pair of intermediate compartments having a first compartment and a second compartment; said cathode assembly comprising a cathode and a bipolar ion exchange membrane, said bipolar ion exchange membrane having a cation exchange side and an anion exchange side; said anode assembly comprising a hydrogen consuming gas diffusion anode and a current collecting electrode; said first compartment and said second compartment of said pair of intermediate compartments are separated from each other by an anion exchange membrane, said first compartment being defined by said anion exchange side of said bipolar ion exchange membrane and said anion exchange membrane, said second compartment being defined by said anion exchange membrane and said hydrogen consuming gas diffusion anode; provided that when said electrolytic cell has more than one pair of intermediate compartments, each pair of intermediate compartments is separated from its adjacent pair of intermediate compartments by an intermediate bipolar ion exchange membrane having a cation exchange side located on the side of said intermediate bipolar ion exchange membrane that is closer to said catholyte compartment and an anion exchange side located on the side of said intermediate bipolar ion exchange membrane that is closer to said anode compartment.

23. The electrolytic cell of claim 22 wherein said anode assembly further comprises a hydraulic barrier, said hydrogen consuming gas diffusion anode being fixedly held between said hydraulic barrier and said current collecting electrode, and said second compartment of said pair of intermediate compartments is separated from said anode compartment by said hydraulic barrier.

24. The electrolytic cell of claim 23 wherein said hydraulic barrier is a cation exchange membrane.

* * * * *